United States Patent
Godwin, Sr.

(10) Patent No.: US 12,125,579 B2
(45) Date of Patent: Oct. 22, 2024

(54) MIRROR IMAGE APPS DEVICE COMPRISES PLURALITY OF SENSORS ACQUIRE VIDEO AND AUDIO DATA TO DETERMINE FIRST EXPRESSION, SOFTWARE AND SYSTEM, AND METHODS OF OPERATING SAME

(71) Applicant: David A. Godwin, Sr., Egg Harbor Township, NJ (US)

(72) Inventor: David A. Godwin, Sr., Egg Harbor Township, NJ (US)

(*) Notice: Subject to any disclaimer, the term of this patent is extended or adjusted under 35 U.S.C. 154(b) by 435 days.

(21) Appl. No.: 17/518,754

(22) Filed: Nov. 4, 2021

(65) Prior Publication Data

US 2022/0148706 A1     May 12, 2022

Related U.S. Application Data

(60) Provisional application No. 63/112,565, filed on Nov. 11, 2020.

(51) Int. Cl.

| | |
|---|---|
| *G16H 20/70* | (2018.01) |
| *G06V 40/16* | (2022.01) |
| *G16H 40/67* | (2018.01) |
| *G16H 80/00* | (2018.01) |
| *G06V 40/18* | (2022.01) |
| *G06V 40/70* | (2022.01) |

(52) U.S. Cl.
CPC ........... *G16H 20/70* (2018.01); *G06V 40/174* (2022.01); *G16H 40/67* (2018.01); *G16H 80/00* (2018.01); *G06V 40/16* (2022.01); *G06V 40/197* (2022.01); *G06V 40/70* (2022.01)

(58) Field of Classification Search
None
See application file for complete search history.

(56) References Cited

U.S. PATENT DOCUMENTS

| | | | |
|---|---|---|---|
| 10,346,675 B1* | 7/2019 | Nagalla | G06V 40/172 |
| 2017/0221484 A1* | 8/2017 | Poltorak | G10L 15/142 |
| 2020/0005781 A1* | 1/2020 | Qiao | G10L 15/22 |
| 2020/0074155 A1* | 3/2020 | de Paula | G06V 40/174 |
| 2020/0151439 A1* | 5/2020 | Johnson | G06V 40/166 |
| 2020/0226239 A1* | 7/2020 | Leuthardt | H04L 63/0861 |

* cited by examiner

*Primary Examiner* — Haris Sabah
(74) *Attorney, Agent, or Firm* — Neil A. Steinberg

(57) ABSTRACT

An Mirror Image Apps, system and method of operation. A method of monitoring a Client, via an MIA process using an MIA device, the method includes (i) presenting predetermined images, self-portraits, statements, music, and/or questions, via an MIA device, to a Client associated with the MIA device, while the Client is alone, (ii) acquiring video and/or audio data, via the MIA device, of the Client's responses to the predetermined images, self-portraits, statements, music, and/or questions presented to the Client via the MIA device, (iii) analyzing the video and/or audio data, and/or changes therein, to detect the state of the Client, and (iv) determining a course of action, via a Core Group associated with the Client, for treatment of the Client based on the analysis of the video and/or audio data.

20 Claims, 7 Drawing Sheets

MIRROR IMAGE APPS DEVICE COMPRISES PLURALITY OF SENSORS ACQUIRE VIDEO AND AUDIO DATA TO DETERMINE FIRST EXPRESSION, SOFTWARE AND SYSTEM, AND METHODS OF OPERATING SAME

RELATED APPLICATION

This non-provisional application claims priority to and the benefit of U.S. Provisional Application No. 63/112,565, entitled "Mirror Image Apps Device and System, and Methods of Operating Same", filed Nov. 11, 2020. The '565 provisional application is hereby incorporated herein by reference in its entirety.

INTRODUCTION

The present inventions are directed to devices including or implementing one or more Mirror Image Apps Device, and systems employing same, and applications and processes based thereon (collectively referred to as "MIA device"). The MIA device is an innovative, integrated hardware and software solution that facilitates detection and analyses of clients/patients/subjects (collectively referred to as "Clients", and singularly/individually as "Client") having or exhibiting, for example, characteristics of psychological disorders or abuse (e.g., co-occurring disorders, mood disorders, process addictions, O.U.D., S.U.D., A.O.D. and/or, substance dependency, addiction or abuse).

Notably, one of the most entwined problems in the mental health field is the assessment of dual disorders (Hazelden Staff, 2016). This is because one symptom may mask another and it may indicate or show confusing symptoms because the Client may not contribute or attribute one symptom with the other symptom, or accept its presence, without the evidence to back it up. The soft data may be useful or needed to help the Client make this choice (Hazelden Staff, 2016). The soft data that may be understood by the Client as well as the physician in charge.

MIA device, and software thereof and processes implemented thereby (collectively referred to as "MIA device/software"), are non-intrusive and non-invasive. In one embodiment, the MIA device/software introduces each Client to themselves as if they are speaking into a mirror—for example, early morning or late night when the Client is alone (e.g., without one or more members of the Core Group (e.g., counselors) or intervention from family). In another embodiment, the MIA device/software, while in use, detects the Client is in distress, agitated and/or nearing, entering and/or in a geographic area that causes, triggers or induces distress, agitation or harmful activity (e.g., drug usage). In response the MIA device/software advises the Client, for example, physically, visually and/or audibly (e.g., vibration or sound (e.g., chime)) when the Client is nearing, entering and/or in such a geographic area, and, in addition, requests or instructs the Client to pause and, for example, rethink or reconsider the behavior or actions before proceeding/continuing given the situation or circumstances. In addition, the MIA device/software may notify the Core Group that the Client is in distress, agitated and/or nearing, entering and/or in a geographic area that causes, triggers or induces distress, agitation or harmful activity (e.g., drug usage). The MIA device/software, in one embodiment, suggests, requests and/or instructs the Client to pause to allow the Client to assess either a flag scenario or a options to avoid the distraction/trigger/distressful situation, for example, by way of Biblical intervention, advice, and/or words of wisdom that suit the situation (e.g., avoid a known or favorite bar, strip club, high drug traffic area, ex-relationship, previous job site or colleague, etc.).

The MIA device/software may also alert or notify the Client's counselor, therapist, medical professional, staff support group and/or director (collectively referred to herein as "Core Group") thereby allowing the Core Group an opportunity to intervene and/or assist the Client without requiring the Client, for example, to actively or pro-actively contact the Core Group. Thus, in one embodiment, the MIA device/software may contact the Core Group and advise the Core Group of one or more (or all) of the circumstances or situation that initiated or caused the intervention by the MIA device/software. As such, the Client simply needs to engage or answer to one or more members of the Core Group, for example, via video and/or audio communication provided by the MIA device/software.

The MIA device/software employs or is premised on a Mirror Effect. Here, the MIA device/software allows the Client to talk to and interact with MIA device, as if they are looking into a mirror. The program in which MIA device is being used allows the Client to interact with themselves or engage themselves while the MIA device/software acquires data for analysis. The MIA device may be used in privacy of their home or residential program, clinical trial/testing or remotely therefrom (e.g., on the go such as in out-patient, PHP, IOP). The MIA device detects physical (e.g., facial) characteristics (and/or changes therein), non-verbal communication or cues, cultural nuances, socially evolved mannerisms, tic(s), and/or voice or speech data (e.g., tone, frequency and/or pattern; and/or changes therein) of the Client, processes one, some and/or all of such data to detect, identify, assess and/or analyze a Client having or exhibiting certain behavior, for example, suicidal ideations, bi-polar episodes, major depression, anxiety, PTSD and forms of agitation, distress, trauma and/or addiction and/or mood disorders listed in the DSM-5.

BRIEF DESCRIPTION OF THE DRAWINGS

The present inventions may be implemented in connection with embodiments illustrated in the attached drawings. These drawings show different aspects of the present inventions and, where appropriate, reference numerals illustrating like structures, components, materials and/or elements in different figures are labeled similarly. It is understood that various combinations of the structures, components, and/or elements, other than those specifically shown, are contemplated and are within the scope of the present inventions.

Moreover, there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended to reflect or indicate the embodiment(s) is/are "example" embodiment(s).

FIGS. 4A and 4B illustrate, in block diagram form, an MIA device mounted or fixed (e.g., temporarily or permanently), via a bracket, to a wall as an exemplary Stand-Alone configuration or embodiment, wherein FIG. 4B is a cross-sectional view of FIG. 4A along line A-A;

Figure 1:
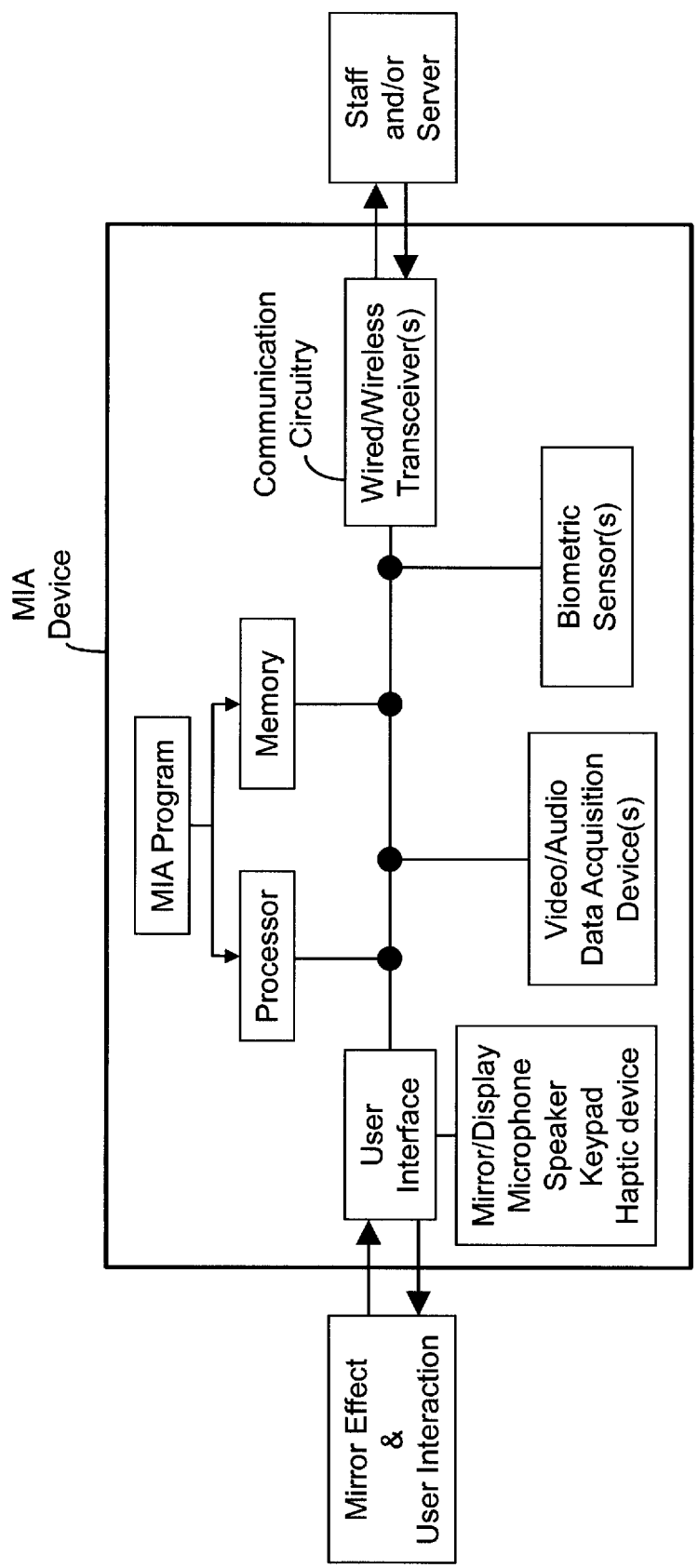
FIG. 1 illustrates, in block diagram form, an exemplary embodiment of a MIA device, according to certain aspects of the present inventions, including a user interface (e.g., a mirror, display, microphone, speaker, keypad and/or haptic vibration device), a processor to implement MIA programs/applications, video and/or audio data acquisition devices to acquire data representative of the Client interaction (e.g., verbal, physical and/or facial), biometric sensors to collect other data of the Client, communication circuitry (e.g., wired or wireless transceiver(s)), according to certain aspects and embodiments of the present inventions.

Again, there are many inventions described and illustrated herein. The present inventions are neither limited to any single aspect nor embodiment thereof, nor to any combinations and/or permutations of such aspects and/or embodiments. Each of the aspects of the present inventions, and/or embodiments thereof, may be employed alone or in combination with one or more of the other aspects of the present inventions and/or embodiments thereof. For the sake of brevity, many of those combinations and permutations are neither illustrated nor discussed separately herein.

DETAILED DESCRIPTION

The present inventions relate to devices, systems and techniques including or implementing one or more Mirror Image Apps, and applications and processes based thereon (as noted above, collectively referred to as "MIA device"). The MIA device is an innovative, integrated hardware and software solution that facilitates detection and analyses of Clients/patients/subjects having or exhibiting, for example, characteristics of abnormal physiological and/or psychological disorders or abuse (e.g., co-occurring disorders, mood disorders, process addictions, O.U.D., S.U.D., A.O.D. and/or, substance dependency, addiction or abuse).

MIA device, and software thereof and processes implemented thereby (as noted above, collectively referred to as "MIA device/software"), are non-intrusive and non-invasive. In one embodiment, the MIA device/software introduces each client/patient/subject (as noted above, collectively referred to as "Client") to themselves as if they are speaking into a mirror—for example, early morning or late night when the Client is alone (e.g., without one or more of the Core Group or intervention from family). In another embodiment, the MIA device/software detects or is notified that the Client is in distress, agitated and/or nearing, entering and/or in a geographic area that causes, triggers or induces distress, agitation or harmful activity (e.g., drug usage). In response the MIA device/software advises the Client, for example, physically, visually and/or audibly (e.g., vibration or sound (e.g., chime)) when the Client is nearing, entering and/or in such a geographic area, and, in addition, requests or instructs the Client to pause before proceeding/continuing given the situation or circumstances. In addition, the MIA device/software may request or instruct the Client to pause to allow the Client to assess either a flag scenario or a options to avoid the distraction/trigger/distressful situation (e.g., avoid a known or favorite bar, strip club, high drug traffic area, ex-relationship, previous job site or colleague, etc.).

The MIA device/software may also alert or notify one or more members of the Client's Core Group thereby allowing one or more members of the Core Group an opportunity to intervene and/or assist the Client without requiring the Client, for example, to actively or pro-actively contact the Core Group. Thus, in one embodiment, the MIA device/software may contact the Core Group and advise the Core Group of one or more (or all) of the circumstances or situation that initiated or caused the intervention by the MIA device/software. As such, the Client simply needs to engage or answer to the Core Group, for example, via video and/or audio communication provided by the MIA device/software or as designated by the Core Group, attend the next meeting or reporting date. Providing the resident members of the Core Group or remote members of the Core Group access to data, alerts and/or notifications (or other valuable insight) before meeting or interaction with the Client may improve assessment of behavior(s) of the Client and/or suggest modifications or changes in a treatment plan of or future interactions with the Client.

The MIA device employs or is premised on a Mirror Effect. Here, the MIA device/software allows the Client to talk to and interact with MIA device, as if they are looking into a mirror. The program in which MIA device is being used allows the Client to interact with themselves or engage themselves while the MIA device/software acquires data for analysis. This analysis, in one embodiment, is based on the Client's unique non-verbal communication(s) and/or idiosyncrasies The MIA device may be used in privacy of their home or residential program, clinical trial/testing or remotely therefrom (e.g., on the go such as in out-patient, PHP, IOP). The MIA device detects physical (e.g., facial) characteristics (and/or changes therein), non-verbal cues, cultural nuances, socially evolved mannerisms, tic(s), and/or voice or speech data (e.g., tone, frequency and/or pattern; and/or changes therein) of the Client, processes one, some and/or all of such data to detect, identify, assess and/or analyze a Client having or exhibiting certain behavior, for example, suicidal ideations, bi-polar episodes, major depression, anxiety, PTSD and forms of agitation, distress, trauma and/or addiction and/or mood disorders listed in the DSM-5.

Indeed, in one embodiment, the MIA device/software may be configured to adapt to differences or changes in different societies or cultures—for example, people, societies and/or cultures of the Western Hemisphere or people, societies and/or cultures that are different therefrom (e.g., traits or characteristics of people, societies and/or cultures of the Southern Hemisphere). For example, the MIA device/software may be manually or automatically (e.g., based on location data) configured to detect, identify, assess and/or analyze a Client having traits or characteristics of people, societies and/or cultures in which the MIA device/software is employed thereby facilitating country/state/city interaction and/or providing improved operation based on country/state/city interaction.

With reference to FIG. 1, the MIA device, in one embodiment, includes a display, a speaker, an audio sensor (e.g., microphone), a video sensor (e.g., camera), a processor and software/program. In operation, in one embodiment, the MIA device presents to the Client, for example, when the Client is alone, images, self-portraits, statements, music, and/or questions (or the like) to the Client via, for example, the display and/or speaker. The Client responds to such images, statements, music, and/or questions. Here, the camera and/or the microphone detects the response and provides the input to the processor. The processor may analyze the facial characteristics (and/or changes therein) and/or voice or speech data (e.g., tone, frequency and/or pattern; and/or changes therein) of the Client. These analyses may be recorded and shared with the treatment team at all times including being graded or classified, for example, by action, severity or concern. In one embodiment, the MIA device and system may employ a one or more flag indications (red, blue, green, etc.). The Client's response to such images, statements, music, and/or questions will help one or more of the Core Group to better assess the flags, if any, and make on real time changes in healthcare/treatment plan. The analysis may be performed based on one or more of the aforementioned criteria, category or the like (e.g., facial characteristics, in view of voice and/or speech data, and in further view of the questions). These criteria will be a product of the test being given or detailed interaction initiated by MIA device/software based on data and/or analysis (which may include current or previous MIA device engagements (e.g., previous data and analyses by an MIA device)), one or more of the Core Group, e.g., a counselor, therapist, director or medical professional, may determine, prescribe and/or implement a course of action in relation to the Client.

Figure 2B:
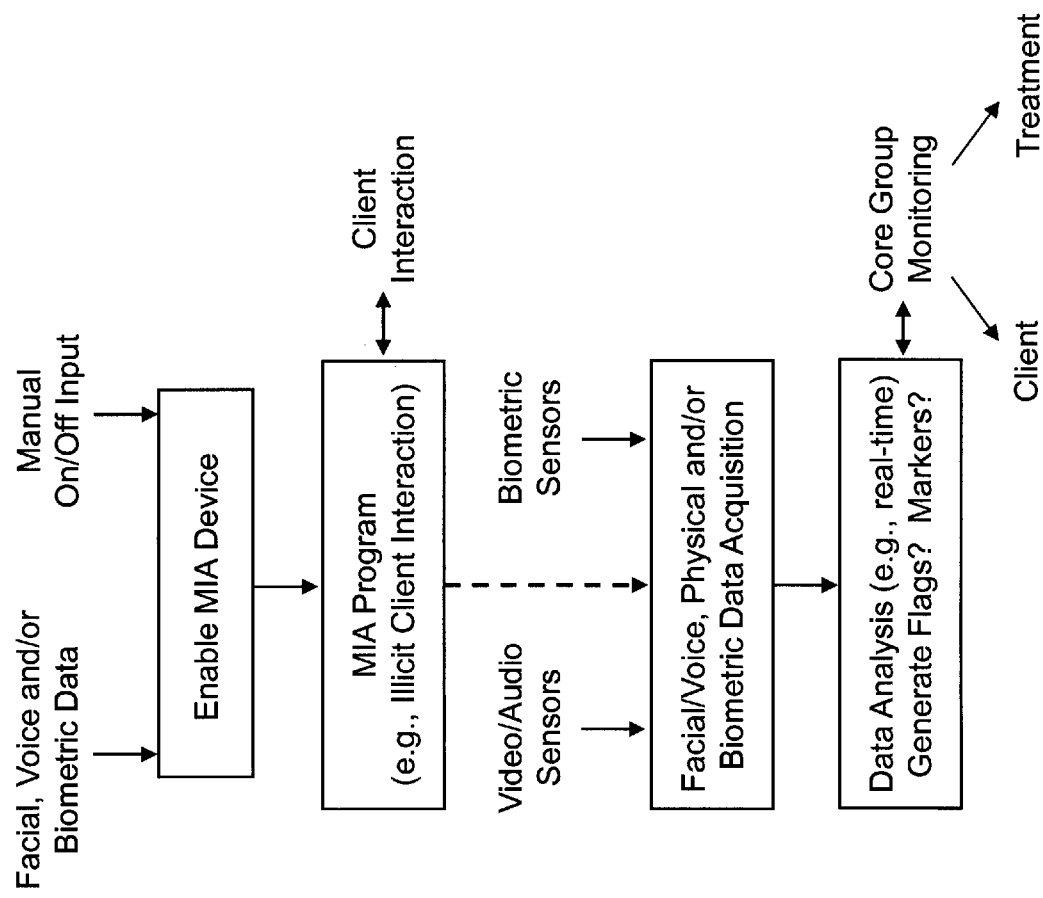
FIG. 2B illustrates an exemplary flow or operation of a Client interacting with an MIA device (e.g., as illustrated in FIG. 2A), according to certain aspects of the present inventions, wherein, the Client may enable the MIA device manually (via, e.g., an on/off or proximity sensor switch) and/or the Client may engage the MIA device via facial, voice and/or biometric sensors which, upon detecting/authenticating the Client, may enable Client interaction with the MIA device; thereafter, the MIA program of the MIA device may interact with the Client wherein video, audio and/or biometric sensors may detect, for example, facial, voice, physical and/or biometric responses, changes and/or actions (data acquisition) and provide such data to processor(s) to analyze the data (e.g., in real-time or post-interaction), according to certain aspects of the present inventions; in one embodiment, the MIA program data is also provided to the processor and correlated with the video, audio and/or biometric data, for example, facial, voice, physical, and/or biometric responses, changes and/or actions (data acquisition) to analyze such data in the context of the MIA program data (e.g., in real-time or post-interaction), according to certain aspects of the present inventions; markers may be embedded within the raw and/or processed data and/or flags (e.g., having certain severity/meaning) may be generated based on the analyses; the data (raw and/or analyzed data), markers and/or flags (if any) may be transmitted to one or more of the Core Group (resident or remote) that is monitoring the interaction (e.g., in real-time or post-interaction) wherein such member may, for example, engage the Client (e.g., via therapy) and/or propose healthcare/treatment and/or changes therein, according to certain aspects of the present inventions.
Figure 2A:
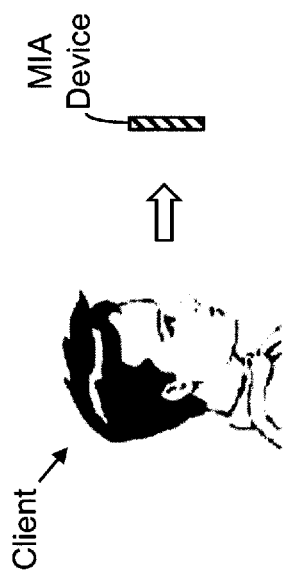
FIG. 2A is an illustration of a Client interfacing with an MIA device, according to certain aspects of the present inventions.

With continued reference to FIGS. 1, 2A and 2B, the MIA device/software may acquire or record video of the interaction(s) of the Client and store the video on memory resident in the device and/or on a closed network. For example, in one embodiment, the Client may enable the MIA device manually (via, e.g., an on/off or proximity sensor switch) and/or the Client may engage the MIA device via facial, voice and/or biometric sensors which, upon detecting/authenticating the Client, may enable Client interaction with the MIA device. Thereafter, the Client may communicate (verbally or non-verbally) or interact with the MIA device/software which may record or acquire data, via video, audio and/or biometric sensors, of such communication and/or interaction. For example, the MIA program of the MIA device may induce the Client's interaction wherein video, audio and/or biometric sensors may detect, for example, facial, voice, physical, and/or biometric responses, changes and/or actions (data acquisition) and provide such data to processor(s) to analyze the data (e.g., in real-time or post-interaction). In one embodiment, the data of the MIA program is also provided to the processor and correlated with the video, audio and/or biometric data, for example, facial, voice, physical, and/or biometric responses, changes and/or actions (data acquisition) to analyze such data in the context of the MIA program data (e.g., in real-time or post-interaction). Markers may be embedded within the raw and/or processed data and/or flags (e.g., having certain severity/meaning) may be generated based on the analyses.

Figure 2C:
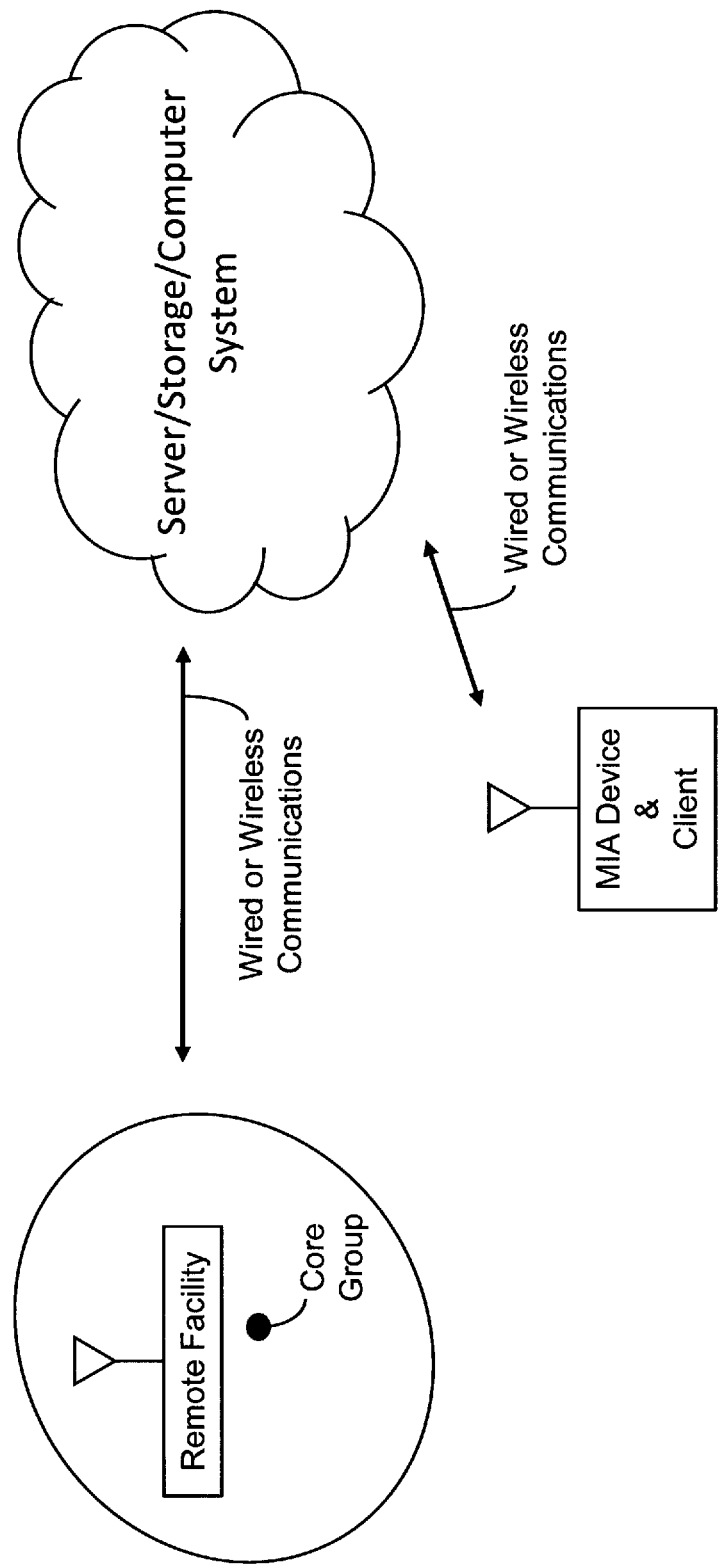
FIG. 2C illustrates a block diagram of an exemplary embodiment of a system, according to one or more aspects of the present inventions, including an MIA device (and Client) communicating with a remote facility, including a monitoring device (and one or more of the Core Group), via the internet.

With reference to FIG. 2C, the data (raw and/or analyzed data), markers and/or flags (if any) may be transmitted to one or more of the Core Group (resident or remote) that is monitoring the interaction (e.g., in real-time or post-interaction). That is, the acquired video, audio and/or biometric data may also be written to and stored in storage device of cloud-based design. This data/video-footage/test results, etc. may be stored in the cloud (i.e., a remote server and/or storage device) to facilitate access remotely (via, for example, one or more of the Core Group (e.g., one or more directors, therapists, counselors, specialists and/or staff—whether resident to or remote from the Client) wherein such Core Group member(s) may, for example, engage the Client (e.g., via therapy) and/or propose healthcare/treatment and/or changes. Indeed, in one embodiment, this information will be shared with one or more of the Core Group that is, for example, within the network assigned to individual facilities and/or Clients of the institution or program and/or between one or more of those within the Core Group—whether within and/or without the state, within the network of the Core Group (e.g., contracted specialist and/or employed staff) via, for example, one or more telehealth applications. The MIA device may be suitably programmed to administer one or more of test, for example: Substance Abuse Screening Instruments such as The Drug Abuse Screening Test (DAST) which is a 28-item self-report scale and The Michigan Alcoholism Screening Test (MAST) also a self-reporting scale, Minnesota Multiphasic Personality Inventory (MMPI) which has some 567 true/false questions and different versions that can be asked over a progressive period of time to compile the information along with several other assessment tools simultaneously. Notably, to establish a baseline the MIA device/software may use tools such as Substance Abuse Subtle Screening Inventory (SASSI) and/or The Behaviors & Attitudes Drinking & Driving Scale (BADDS). Other tests, in addition thereto or in lieu thereof, may also be administered by the MIA device/software including: the Alcohol Use Disorder Identification Test (AUDIT), The Texas Christian University Drug Screen II (TCUDS II), Beck Depression Inventory-II, The Mini-International Neuropsychiatric Interview (M.I.N.I.) and other tools which are used by member(s) of the Core Group dependent of the selected facility.

Notably, the MIA device/software may also include a biometric sensor (e.g., blood pressure sensor, eye scanner and/or fingerprint sensor) to verify the Client and/or scan, measure, collect and output current biological data of the Client (e.g., blood pressure/oxygen heart rate, glucose level, etc.). (See, FIG. 1). That data may be maintained in the MIA device as well as uploaded to one or more of the Core Group to facilitate accurate record keeping and to better assess the daily, hourly changes through the software to determine mental health and stability and identify and detect changes (e.g., improvement or decline) of mental health and stability.

The MIA device/software may be suitably programmed to work with clinical testing such as a blind and a double blind test. Tests where interaction with the subject is crucial in the soft data analysis is needed for the controversial long-term effects of marijuana, vapes and designer drugs that are or may come into the field of study.

Figure 3:
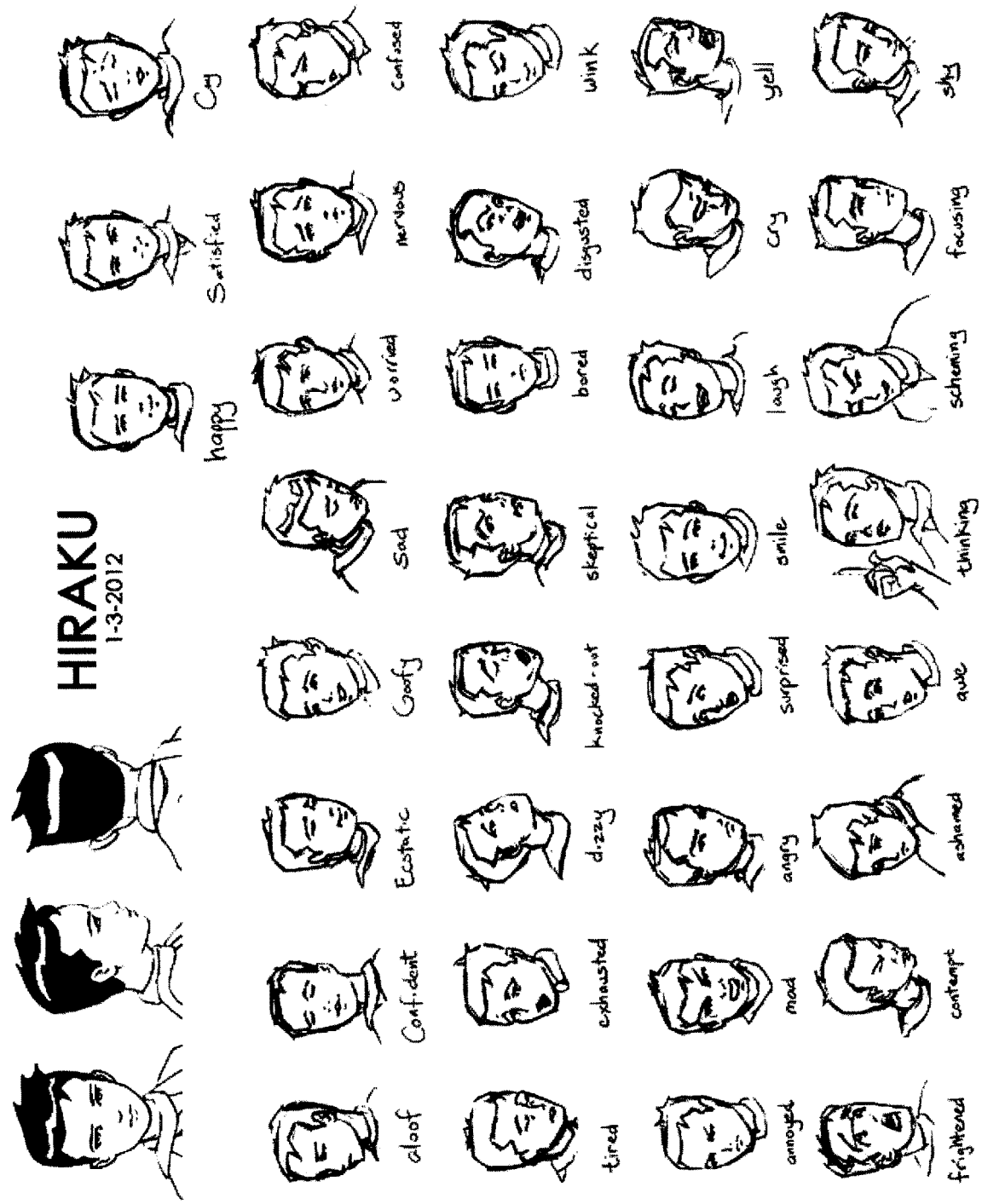
FIG. 3 is an illustration of exemplary facial expressions of a Client that are measured and analyzed by an MIA device, system including an MIA device, a monitoring device in communication with an MIA device (see, e.g., FIG. 2B), according to certain aspects of the present inventions.

The MIA device is programmed to learn (i.e., Machine Learning (ML)) from each ethnic encounter and or subculture interaction by categorizing the 1st, 2nd, 3rd, etc. generation and placement, socioeconomic induced answer to key questions in the MIA device's/software's learning phase and build upon these interactions as well as cultural nuances of each individual case/individual. The MIA device's/software's Machine Learning (ML) capability will allow searches of internet interaction to best categorize said nuances for future identity of non-verbal communication and combinations with verbal interaction, for example, after a base or foundation has been established. A network of base study may be performed and/or acquired from each MIA device interaction with the Client providing a cluster of information for the ML to employ. Kinesics has five types of language and they are Emblems, Regulators, Illustrators, Affective Display, and Adaptors which all have different meanings in different cultures. Therefore, the MIA device/software will focus heavily on regulators (e.g., non-verbal communications) and affective display in facial recognition programming for better understanding in the ongoing assessing of each Client. (See FIG. 3 wherein the Client may exhibit a plurality of facial expressions). The MIA device/software may also impact or focus on regulators and effective other displays in body recognition programming for improved understanding in the ongoing assessment of a Client associated with the MIA device/software when employing the Stand-Alone device.

Notably, most if not all non-verbal cues, actions or facial expressions are contributed to the Anglo-Saxon and/or European model of facial expressions. By using the machine learning (ML) and artificial intelligent (AI) sensitivity of MIA, these Kinesics images will be corrected and afford a better understanding of Client through the lens of each Client's culture/subculture, ethnical background, etc., and up-bringing as they speak and interact with their image and hear their tone of voice reflected back at them during sessions. These assessments may be gathered via the internet that may be searched by the machine learning design of and implementation in the MIA software.

Indeed, in one embodiment, the machine learning capability is an active progressive part of the MIA device/software for building rapport and interacting conversation with Clients allowing one or more of the Core Group a benefit of understanding the nuances, idiosyncrasies and behavior, and changes therein over time (e.g., between uses of the MIA device/software) from a cultural point of view through the video Cliff notes before individual sessions begin. Giving more time for better focused diagnostic cognitive therapy. By doing so, the MIA device/software may also ease the tension of the Client before interacting with the one or more of the Core Group (e.g., counselor) by alleviating anxiety of first meetings and uncomfortable discussions of past trauma/fears and/or desires of the Client. Allowing the Client to speak in a safe place will allow for better integrity in sessions. Giving time for the Client to speak openly without time restraints unless given a specific task to perform/complete (i.e. assessment tests, mood test, meditation, etc.).

The MIA device/software, and system including same, in one embodiment, may generate, identify and/or separate "black flags" which will indicate immediate intervention (suicide ideations/plans, viable threat to harm others, harm that has already taken place, e.g., kidnapping, murder, sexual abuse, etc.), "red flag" severe situations needing immediate attention, "blue flags" cause for further analysis on mental stability e.g. Mental Status Exam (MSE), "green flags" points of improvement in treatment and conversation, "orange flags" further OUD, SUD, AOD analysis is needed, "yellow flags" subjects where avoidance shows barriers or blockage and caution is needed as well as other key points in the interactions. "White flags" may also be implemented and, in this embodiment, will indicate a need to implement, reconsider and/or change a treatment plan and/or termination of program due to lack of or insufficient participation or engagement by the Client (whether overall or during one or more particular periods of time). In one embodiment, use of the MIA device/software by the device includes set times for interaction/conversation/meditation, etc. However, in addition thereto, the MIA device may be activated by one or more of the Core Group if needed to send for help (chip locator) or be used to call/text or ping the Client to speak with a member of the Core Group (e.g., counselor) without a set appointment. These flags are features or components of MIA device's/software's "advance warning system" so once a Client starts to interact with the MIA device/software the recording (video and/or audio) cannot be changed, modified, manipulated and/or coerced. The recording may be stored in two locations (locally (e.g., in house) and remotely (e.g., in the cloud)). In one embodiment, first impressions are used (e.g., all that is used) so each interaction is unique and a first.

In another embodiment, in addition to collecting, acquiring and/or gathering information, the MIA device/software will provide Practical Biblical insight or guidance to inspire and motivate as well as rebuff the Client's way of thinking (CBT) in daily impartations of encouragement through biblical messages but without biblical addresses such as chapter and verse. For example, the version of Biblical conversation may be tailored by the MIA device/software best suited for the Client's intellectual outlook (Message Bible vs King James). This along with moments of meditation where biblical reminders of self-awareness, healing and purpose of life will be streamed to the Client via videos/music/writings as well as reproof for correction in cognitive behavior, positive reinforcement, and negative reinforcement. The MIA device/software will also prompt the Client to perform exercises to increase cognitive awareness and positive thought processing for day to day events and activities, e.g. looking into mirror of the MIA device/software and repeating, "I am made in the Image and Likeness of God and He likes me very much" to the sound of music or tune that suggest hope and strength in the Client's culture preference as they do the exercise. Notably, this embodiment is not intended to sway nor is it presented to disrupt the flow of treatment and can be used as an opportunity or a springboard for conversation during the sessions between a member of the Core Group (e.g., counselor) and Client. Assignments can be given as a daily study guide for the duration of the Client's participation in residential treatment, Outpatient treatment, IOP and/or other timeframes where the Client/patron will use the MIA device/software to build a Christ-Centered lifestyle and soberminded living.

Figure 4B:
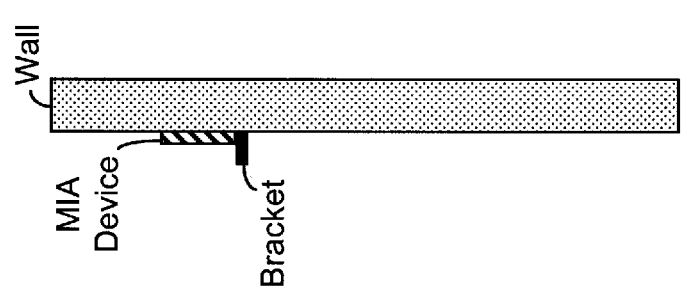
Figure 4A:
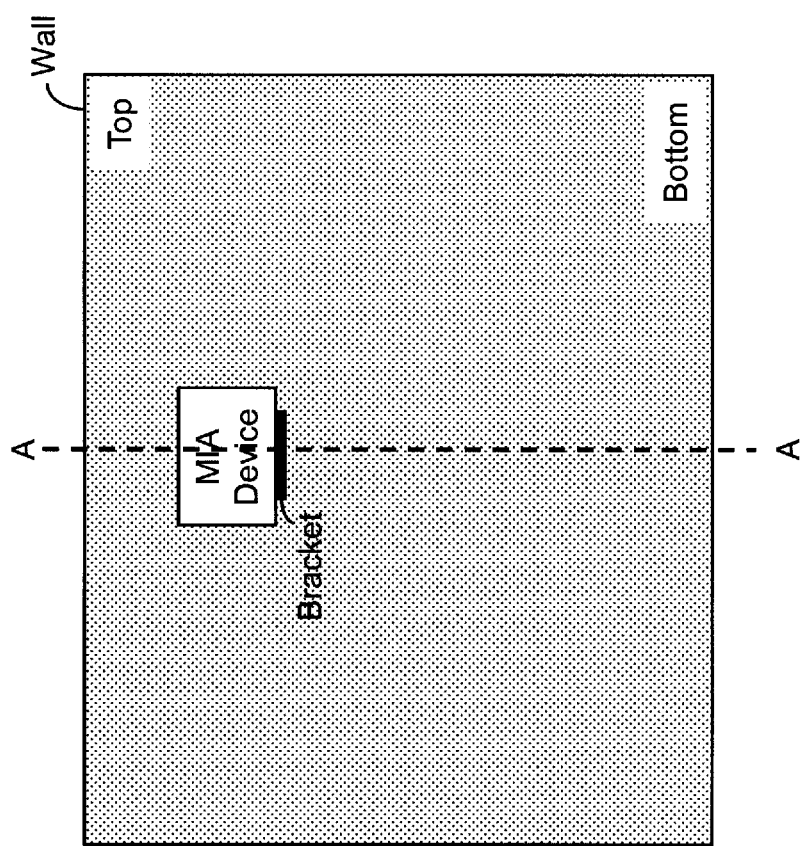

In another embodiment, the Mirror Image Effect of the "Stand-Alone" device will allow for an avatar to be present within and displayed on the mirror or display of the MIA device that will be a target or focus of conversation as the Client openly speaks to the mirror of the MIA device. The MIA device/software may collect or gather more "full body" movement from and activity of the Client to, for example, improve grasp the intensity or subtle movements of the Client as they engage or operate the MIA device and, for example, converse about the events going on in their lives. The "Stand Alone" device may be employed by Clients that may have disabilities (e.g., physical and/or psychological) and are without the use of their hands or unable to keep in line with the facial focus of MIA device's camera, mirror or screen or within a room of, for example, a residence where the MIA device may be fixed to a wall thereof (i.e., as a "Wall unit"). In this way, the MIA device is better suited for the purpose of Client's sessions. The Stand-Alone is also available to be used in resident programs. (See, FIGS. 4A and 4B).

In one embodiment, the Stand-Alone may be implemented via brackets placed on wall units in, for example, private areas for the Client to have private moments to express themselves freely as they look within the mirror of the MIA device. Notably, the Stand-Alone may also be integrated into existing workout exercise equipment wherein the software of the MIA device/software may be incorporated into existing workout exercise equipment and the monitor and camera of that equipment may be employed in lieu of similar hardware described above. Here, such an embodiment may be implemented into equipment presently on the market or those that will come hereafter.

The interaction or test of the MIA device may be tailored, changed and/or selected to suit or accommodate the facility or agency associated therewith and/or the information/data sought by one or more of the Core Group (e.g., resident or remote staff or administration) of any clinical diversity in which soft-data or psychological information can be collected and categorized. These categories, and/or information related thereto, may be viewed or presented in Cliff notes of video acquired by the MIA device/software. In addition thereto, or in lieu thereof, the categories, and/or information related thereto, may be provided or viewed in a streaming presentation (e.g., fully streamed) for teaching and educational purposes, correction and encouragement of Clients (i.e. timeline, first day footage, etc.). Having the MIA divide the stream into sections/chapters (e.g., month to month, week to week, day to day, or hour by hour changes). In one embodiment, these Cliff notes may be available to the Core Group and may be observed on equipment on the Core Group side of the system or program. This information may be administratively used in a class setting for training and study of difficult cases of substance abuse, substance dependency, mental health issues or Co-Occurring Disorder as well as clinical trials of certain general medicine trials. The changes may be made to reflect the ethnic, cultural, socio-economic class or race/tribe in which the Client is most comfortable as the MIA device/software identifies and makes changes to accommodate for best angle of interaction and recording or acquisition of soft data (e.g., psychological effects/responses, state of mind and/or changes therein).

The MIA device/software is a useful tool for clinical trials within the pharmaceutical industry by data gathering of soft data (e.g., psychological effects/responses, state of mind and/or changes therein) for drugs, such as, for example, anxiety medications, major depression medication, PTSD medication, etc. In one embodiment, the MIA device/software may be available to and accessible by the Client for relatively long periods of time (e.g., 1 month, 3 months, 6 months, or longer) in a home setting (e.g., in the Client's room, apartment, house and/or office or place-of-work) during blind/double blind studies eliminating the need for full observation by one or more of the Core Group. With MIA device/software being an interactive device or tool, it is advantageous for the Client or subject to adhere to the contracted design for the study to best receive results. By viewing, recording and sharing the information through the lens of the MIA device's/software's observation of non-verbal or spoken language input/characteristics (e.g., "body language"), idiosyncrasies, nuances, cultural commonalities that may escape the understanding of one or more of the Core Group and pass the information on by pointed Cliff notes, to appropriate members of the team, specialist and study teams. Drug dependency and study of subjects such as marijuana use and its effects when an individual is in detox and or using marijuana for medicinal or recreational purposes, the effects of those coming off of opioids such as Methadone and suboxone and any other medication or street drug making the MIA device/software a valuable tool for long term studies using the machine learning (ML) and artificial intelligence (AI) software to correctly assess the whys of certain unanswered questions—such as, for example, (i) how does this medication or drug of choice disrupt or correct the Client's ability to live in a positive state of being? (ii) how does the Client perceive their relationship to the medication or drug use? (iii) is it healthy mentally and spiritually within the confines of the Client's culture and if not how does the Core Group (e.g., a counselor) or drug company help adjust by using the soft data to make changes for wholeness of life?

The MIA device/software may modify, supplement and/or augment the presentation (e.g., images, statements, music, and/or questions (or the like)) to the Client based on the hot topics or red flags. In one embodiment, the MIA device/software adjusts the interaction based on one or more earlier responses of the Client (e.g., changes in certain facial characteristics and/or changes in voice or speech data—such as tone, frequency and/or pattern). In another embodiment, the adjustments may be implemented by a member of the Core Group (e.g., an operator or counselor) overseeing the operation of the MIA device—for example, in view of one or more external inputs (e.g., information from a third person—such as a mother, father, wife, girlfriend, child and or specialist in the area of importance to Client's well-being). Making adjustments by placing key words or phrases into the artificial intelligence (AI) for better learning capability (e.g. death of wife/husband, separation of wife/husband, infidelity of wife/husband, etc.) allowing for the MIA device/software to search the data stored from multiple areas the MIA device/software has been in connection with additional or previous Clients and scenarios of same culture, tribe, nationality, socioeconomic life style or region within our data banks or via the web/internet.

For example, in one embodiment, the MIA device/software may detect one or more facial characteristics (and/or changes therein) of Client and, based on an input of the MIA device/software and/or a member of the Core Group (e.g., counselor), the MIA device/software may refocus, deviate and/or modify a predetermined presentation of images, statements, music, and/or questions (or the like) to the Client—for example, introduce new or different questions, test or encouragement pertaining to one or more hot topics or red/green/blue (etc.) flags. The MIA device/software may then process the data (e.g., image or voice) acquired by the MIA device/software, which is collected in response to the new or different questions and or test, to detect, identify, assess and/or analyze the Client. Based on that data and/or analysis (which may include current the MIA device/software engagements as well as one or more previous engagements with the MIA device/software from the Learning Processors (e.g., previous data and analyses by the MIA device/software)), a member of the Core Group (e.g., counselor or consortium of in-network counsel, therapist, and/or specialist) that are participating on the Client in questions behalf, may prescribe a course of action in relation to the Client. This will also give the 3D or 4D effect for good counsel (e.g., Proverbs 11:14, AMP). That is, using this information from the consortium and MIA, a member of the Core Group (e.g., counselor) may better use the time given in individual sessions and deal with and confront or reinforce the behavior that needs to be addressed to promote Cognitive change.

Figure 5:
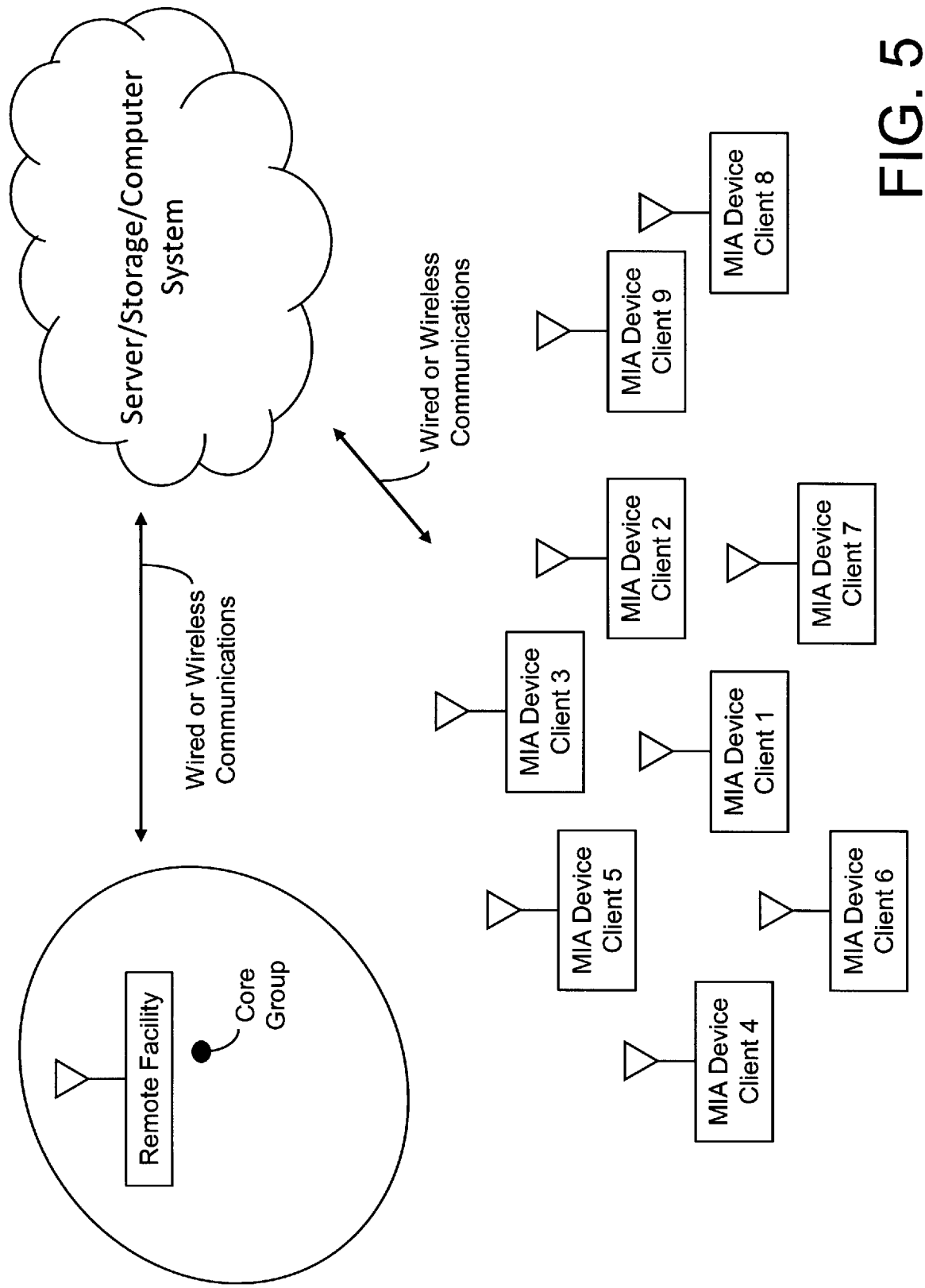
FIG. 5 illustrates a block diagram of an exemplary embodiment of a system, according to one or more aspects of the present inventions, including a plurality of MIA devices (and Clients—each Client associated with a different/separate MIA device) communicating with a remote facility, including a monitoring device (and one or more of the Core Group), via the internet.

During collection of data, or thereafter, the MIA device/software may transmit or forward some or all of the acquired data and any analyses, including (if pertinent) data and/or analyses pertaining to any hot topics or black/white/yellow/red (etc.) flags, to a member of the Core Group (e.g., counselor) or concerned party during clinical trials/programs/IOP, etc. (See, FIGS. 2C and 5). In one embodiment, the MIA device/software provides the data over the internet to a member of the Core Group (e.g., counselor) that is remote from the Client. Being able to use Telehealth measures to cross state boundaries by having a member of the Core Group (e.g., counselor or specialist) co-exist within the MIA system/construct of intimate and numerous connections where the Client can be viewed without biases being introduced by sub-cultures outside the view of the Core Group (e.g., counselor). Here, the connection may be a closed cloud system. This information may be only shared between the Core Group (e.g., clinical site director and their staff) in connection of the trials being performed or counselor(s), therapist on-site or in connection with the team as they build a treatment plan, revisions of treatment or aftercare for said plan—using the data acquired and by the MIA device/software and transmitted to the Core Group (e.g., staff or counselor) for treatment or the like. (See, FIGS. 2C and 5).

The MIA device/software will present assessment data and analyses to staff of the Core Group using test results, facial responses and non-verbal language/information that has been acquired or gathered. In one embodiment, the MIA device/software may also provide or present a suggestion or recommendation toward one or more methods of treatment (e.g., the best methods—which may be ranked) from day one through treatment by continuous assessments of mood, behavior, interaction, conversation and learned information for each Client. This information may be available to local and/or in-network staff of the Core Group and as a starting point from which the Core Group uses, offers and/or recommends for their assessment, making the final call. In this embodiment, the MIA device/software provides unbiased input (i.e., a set of unbiased eyes and ears) regarding a Client that may be resident with the Client, for example, 24/7. All models of evidence based therapeutic treatment may be instigated along with CBT such as MI or harm reduction or person/Client centered, etc. to bring about the changes that may lead to (e.g., the necessary change needed for) the Client's outcome of wholeness.

During operation, the MIA device/software provides a mirror effect, which as stated earlier has a sobering impact on the Client. (See, FIGS. 2A-2C). It enhances the probability that the Client will honestly and fully answer, address and respond to self-images, statements, music, and/or questions (or the like) presented or posed by or interaction with the MIA device/software (i.e., during operation)—that the Client may be hold back, inside or not disclosed under other circumstances. Here, there is no need to immediately build a rapport or go through the trusting phase for the Client. The conversion may be open and unfiltered.

The member of the Core Group (e.g., counselor) may program the MIA device/software to present the Client with images, statements, music, and/or questions (or the like) corresponding to any topic and in any order. For example, the member of the Core Group (e.g., counselor) may program the MIA device/software to present one topic at a time, in a certain order, to pull out information from the Client that may be missed in, for example, a 20 minute session. Gently allowing the member of the Core Group (e.g., counselor) to bring up or introduce topics (in any order or a prescribed order using tools for assessment) that the Client finds intensely disturbing or chaotic and even unspoken culture traits that cannot be spoken about and are expected to be common sense to them. The MIA device/software connects cultures, socioeconomic statuses, where ethnicity or race is not an issue because the MIA device/software may connect the dots (i.e., analyze some or all aspects of the data) for the member of the Core Group (e.g., counselor) and therapist or director to expand their knowledge Client-by-Client, all while collecting soft data along the way for the next Client who uses the MIA device/software in, for example, other regions, countries and/or continents.

The MIA device/software may be used within residential programs or facilities by being linked to a Client through their personal device (e.g., personal computer or tablet). (See, FIG. 5). Allowing for multiple avenues of assessment for less cost and faster results. The MIA device/software, in one embodiment, is hand held for portable use/access or, in another embodiment, may be attached to the wall or stand-alone fixed to a wall as a mirror would be or placed on a shelf to facilitate face level interaction as well as complete body recording. The stand or wall mount of the MIA device/software may be advantageous for those who are challenged with holding the MIA device/software at face level or cultures who speak more with complete body language cues.

Restrictions may be placed on access of the MIA device/software by members of the Core Group (e.g., counselors or directors). For example, in one embodiment, only assigned members of the Core Group (e.g., assigned counselors or staff) of a certain clinic may access the MIA device/software (and the data and analyzes stored or transmitted thereby) for a given Client. This restriction may be used for law enforcement as well as those who would be considered first responders in times of stress. Meaning that MIA device/software may be connected to these first responder institutions when the data and soft data indicate or warrants action outside of the normal assessment where immediate action is needed. For the IOP, PHP or other situations such as troubled youth or adolescents that have the MIA software attached to their phone or device in the private sectors. Allowing the MIA device/software to be incorporated in or a part of the first responders via the AI algorithm. Informing the first responders as well as a member of the Client's Core Group (e.g., counselor or therapist) of any flags that would need to be addressed within a time constraint (e.g., 24 hour/12 hour/6 hour/1 hour window of attention).

Notably, many of the daily activities may be time-sensitive. The completion of these sessions will be part of the contract for compliance of the program and or use of the MIA device/Software in residential or outpatient care (IOP, PHP, Drug Court, etc.) Having Client participation builds the MIA device's/software's ML capabilities as the MIA device/software "learns" the idiosyncrasy, non-verbal language and cultural differences of each individuals, the MIA device/software will categorize like-minded individuals within like-minded subsections to better help one or more members of the Core Group (e.g., counselors) better understand the trauma and level of care needed by said assessment for individual population, culture or subculture. The MIA learning and adaptability will come from the ability to pull information and congruent lifestyles connected to culture/socioeconomic/ethnic people from 1st, 2nd, 3rd and 4th generations within the United States and other countries of origin of Client as well as subcultures within the larger culture. In one aspect, an advantageous aspect of the MIA device/software is the capability to interact within the Worldwide Network Clusters of gathered information from every site algorithm that has signed on from conception. In other words one of the advantages of this embodiment is the reductions of unanswered questions that have occurred in the recent school shootings in just the past several years since a last recent study.

The MIA device/software may be used in Residential, IOP or OP treatment to better provide long term assessment and diagnosing assistance. Further, the MIA device may provide guidance or help for planning treatment of Clients having behavioral disorders as well as substance dependence and abuse issues of substances such as opioids, and psychoactive drugs such as caffeine, alcohol, LSD, nicotine, cannabis, cocaine and process addictions such as gambling, internet, gaming, etc. The MIA device/software may be used in programs that are designed to administer Medically Assisted Treatment (MAT) to better help Clients reduce and ultimately come off of medications such as Methadone, Suboxone and Vivitrol. By providing soft data (e.g., psychological and psychological effects/responses, state of mind and/or changes therein) to understand the process and promote more totally sobriety and minimize lapses and relapses during the drop down phase.

The MIA device includes an artificial intelligent (AI) technology with machine learning (ML) capabilities for cultural idiosyncrasies, verbal and non-verbal cues. Such characteristics and feedback may be missed (e.g., often missed) during interaction with one or more members of the Core Group (e.g., counselors).

Notably, machine learning is an application of AI that provides the MIA device/software the ability to automatically learn and improve from experience without being explicitly programmed in connection with the "learned" material. Machine learning focuses on the development of computer programs that can access data and use it to learn for themselves, via the internet as well as Client study within the closed system. This embodiment of the MIA system may learn and store information from one end of the interview process to the next; meaning from the beginning of subject one (who will be the first person in the Beta test) to the last person who uses the MIA software on any given moment. The storage of learned information may be compartmentalized into sub folders where MIA software from different parts may draw from the information instantaneously as needed. Each algorithm include a separate or unique feed indigenous to the subculture it is most familiar to or with the region/state/culture of use.

The MIA device/software is further programmed to consider socioeconomic differences in tics (e.g., facial), speech (e.g., inflection, timing, studder, word choice) and/or eye movement tracking and interactive programming to improve interactions and analyses of the Client. The MIA may also be a tool to teach one or more of the Core Group (e.g., staff) to observe/see, assess and/or analyze the very "tells" that are hidden in the subconscious of all people. All while looking in the mirror of one's soul (will, thought and emotions). The MIA device/software may also utilize picture coding algorithms to improve explanation of facial personalities of each culture being assessed or treated.

With ubiquitous applications in ministry (e.g., Christian) and the scientific world, the MIA device/software is or provides an evidence based tool which may use Biblical standards as an interactive format for enhancement of daily wellness. While this may be used across several fields in marketing, to allow individuals within the Christian worldview to see each individual ethnicity culture and in subcultures that are outside the western ideology of Christendom. By allowing the MIA device/software to share the fears and strengths of each culture as one world that Christ came and died for.

Our primary goals is still clinical trials and evidence based research to better help those in need, providing soft data to coincide with or dispute the hard data of previous and or future trials. Using the MIA device/software to aid/help those who are removing themselves (through step-down treatment) from Medical Assistant Treatment (MAT) long term use is also a big part of the primary goal. Knowing how to best assist in these areas can be done through the MIA device/software, by allowing medical professionals to witness the effects and fears associated with stepdown methods.

The MIA device/software is designed to use the many tools associated with intake and assessment for alcohol, drug screening and AOD's that can be associated with mental illness; e.g. bipolar disorder, anxiety, depression, etc. This is done by the MIA device's/software's active listening and recording of responses that are prompted through the use of but not limited to Drug Abuse Screening Test (DAST-10) which is a 10 question survey using yes and no answers to yield quick data on drug use of Clients, yet the MIA device/software will stretch this along a period of time so the Client doesn't realize they are being tested which leaves less area for programed answers and thus better results (Advanced Recovery systems, 2017). Using NIDA or the National Institute on Drug Use Screening Tool is another example that is a quick use tool for assessment. Along with many others that are approved as well as those to come in future years.

One advantage of the MIA device/software is the ability to use as much or as little as needed to have multiple observations through on-site and off sight therapists, specialists, etc., that are working on a treatment or diagnosis of the Client. With this in mind, the MIA device connects with specialist or team members across multiple platforms to facilitate implementing the best diagnosis and in turn the best treatment for the Client without passing the Client from building to building and the MIA device places assessment of the testing on multiple levels of testing during time stamped measures.

As noted above, the MIA device/software is an artificial intelligence (AI) capable and AI based system that employs or includes machine learning algorithm(s). In this way, the more the MIA device is used, across platforms, the more the MIA device learns and the more the MIA device may assist in connection with analyses, diagnoses and planning. In one embodiment, the MIA device/software focuses on learning from data accessed and providing insight across these platforms to the Core Group (e.g., counselors, therapist, directors) that are connected to the Client. Even though the MIA device doesn't have the last "say", the MIA device/software does acquire and provide data (e.g., soft data) to give its side of the story. Taking the symptom, signs, yes and no answers, data from all and any test done along with the non-verbal language, nuances, idiosyncrasies of the economical background of the individual and culture ques that are missed and then provide evaluation to those who can look over the data and compare simultaneously with less time at less cost.

Figure 6:
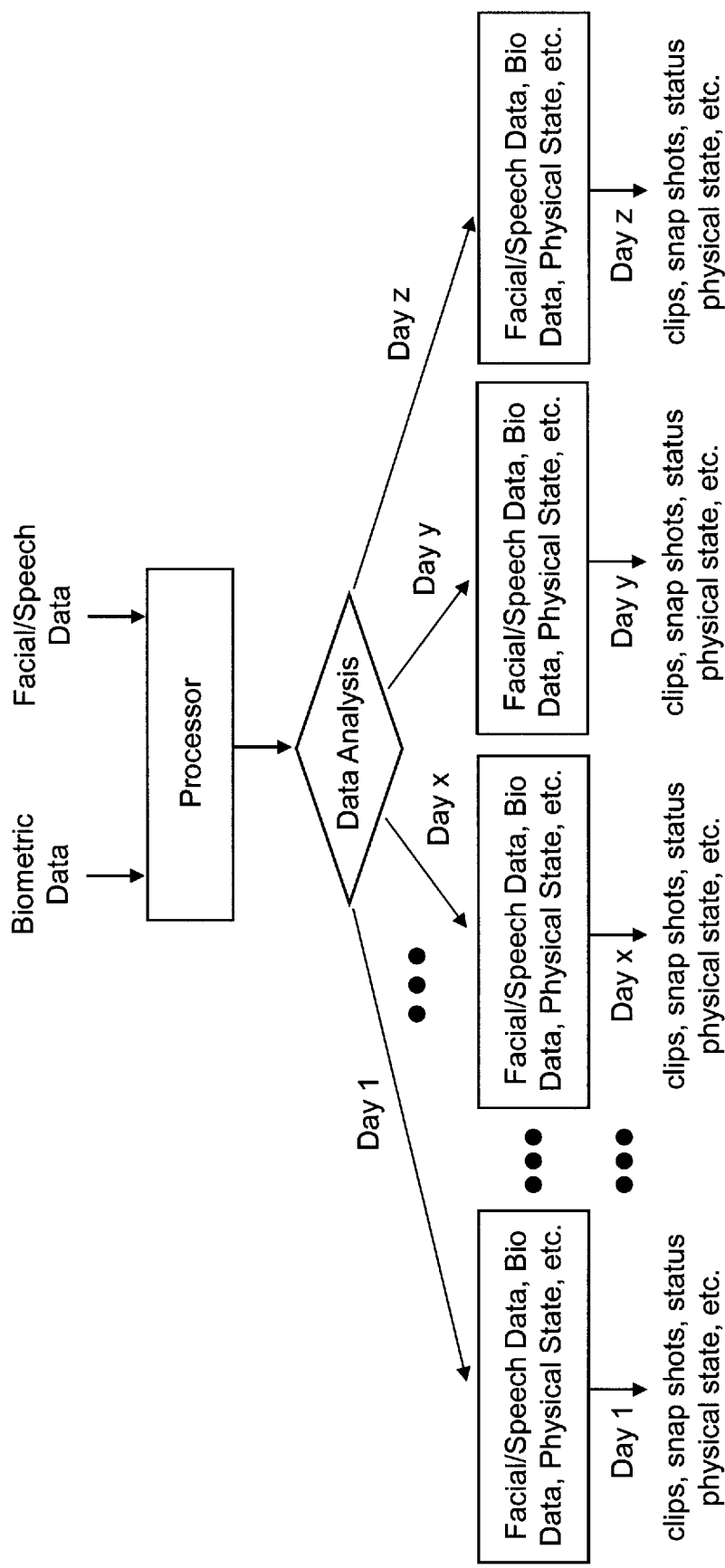
FIG. 6 illustrates a Client's clips, snap shots of their beginning journey (Day 1) to present/current (Day z), along the way the data file may be prepared, compiled and/or presented of the physical changes that come with the Client's recovery, according to certain aspects of the present inventions; notably, the MIA device/software may store such data for review by the Client.

The MIA device/software may store or keep Client's clips, snap shots of their beginning journey to current. Along the way a file may be prepared, compiled and/or presented of the physical changes that come with the Client's recovery. (See, FIG. 6). Building a positive image to coincide with the inner changes of therapy.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the above embodiments of the inventions are merely exemplary. They are not intended to be exhaustive or to limit the inventions to the precise forms, techniques, materials and/or configurations disclosed. Many modifications and variations are possible in light of this disclosure. It is to be understood that other embodiments may be utilized and operational changes may be made without departing from the scope of the present inventions. As such, the scope of the inventions is not limited solely to the description above because the description of the above embodiments has been presented for the purposes of illustration and description.

For example, the MIA device may also include physiological sensor(s) to sense, detect, assess and/or obtain data which is representative of physiologic information of the Client (for example, weight, body fat, blood pressure, pulse rate, blood sugar and the waveform shape corresponding to the heart beat). Moreover, video, audio and biometric sensors may include all permutations and combinations of sensors (for example, one or more physiological sensor(s)). Notably, in one embodiment, processing or analyzing of the data (e.g., video, audio, activity, biometric and/or MIA program data) corresponding to or associated with the Client may be distributed between resident (on-device) circuitry (e.g., a processor resident in the MIA device) and external (off-device) circuitry. (See, FIGS. 2C and 5 wherein the MIA device and the remote facility may include processing or analysis circuitry and/or software to process and analyze the data (e.g., video, audio, activity, biometric and/or MIA program data) transmitted from the MIA device corresponding to or associated with the Client.

In another embodiment, the processing or analyzing of the data (e.g., video, audio, activity, biometric and/or MIA program data) corresponding to or associated with the Client may be entirely via external (off-device) circuitry. (See, remote facility in FIGS. 2C and 5, which includes processing or analysis circuitry and/or software to process and analyze the data (e.g., video, audio, activity, biometric and/or MIA program data) corresponding to or associated with the Client). Here, the processing or analysis circuitry and/or software in the remote facility may in embed markers within the raw and/or processed data and/or generate flags (e.g., having certain severity/meaning) based on the analyses. Thereafter, the data (raw and/or analyzed data), markers and/or flags (if any) may be transmitted to one or more of the Core Group (e.g., resident members of the Core Group) that is monitoring the interaction (e.g., in real-time and/or post-interaction) wherein such member may, for example, engage the Client (e.g., via therapy) and/or propose healthcare/treatment and/or changes therein.

Further, the term "circuitry", means, among other things, a circuit (whether integrated or otherwise), a group of such circuits, one or more processors, one or more state machines, one or more processors implementing software, one or more gate arrays, programmable gate arrays and/or field programmable gate arrays, or a combination of one or more circuits (whether integrated or otherwise), one or more state machines, one or more processors, one or more processors implementing software, one or more gate arrays, programmable gate arrays and/or field programmable gate arrays. The term "data" means, among other things, a current or voltage signal(s) (plural or singular) whether in an analog or a digital form, which may be a single bit (or the like) or multiple bits (or the like).

Importantly, the present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof.

Notably, reference herein to "one embodiment" or "an embodiment" (or the like) means that a particular feature, structure, or characteristic described in connection with the embodiment may be included, employed and/or incorporated in one, some or all of the embodiments of the present inventions. The usages or appearances of the phrase "in one embodiment" or "in another embodiment" (or the like) in the specification are not referring to the same embodiment, nor are separate or alternative embodiments necessarily mutually exclusive of one or more other embodiments, nor limited to a single exclusive embodiment. The same applies to the term "implementation." The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, certain permutations and combinations are not discussed and/or illustrated separately herein.

Further, an embodiment or implementation described herein as "exemplary" is not to be construed as ideal, preferred or advantageous, for example, over other embodiments or implementations; rather, it is intended convey or indicate the embodiment or embodiments are example embodiment(s).

Although the present inventions have been described in certain specific aspects, many additional modifications and variations would be apparent to those skilled in the art. It is therefore to be understood that the present inventions may be practiced otherwise than specifically described without departing from the scope and spirit of the present inventions. Thus, embodiments of the present inventions should be considered in all respects as illustrative/exemplary and not restrictive.

The terms "comprises," "comprising," "includes," "including," "have," and "having" or any other variation thereof, are intended to cover a non-exclusive inclusion, such that a process, method, circuit, article, or apparatus that comprises a list of parts or elements does not include only those parts or elements but may include other parts or elements not expressly listed or inherent to such process, method, article, or apparatus. Further, use of the terms "connect", "connected", "connecting" or "connection" herein should be broadly interpreted to include direct or indirect (e.g., via one or more conductors and/or intermediate devices/elements (active or passive) and/or via inductive or capacitive coupling)) unless intended otherwise (e.g., use of the terms "directly connect" or "directly connected").

The terms "a" and "an" herein do not denote a limitation of quantity, but rather denote the presence of at least one of the referenced item. Further, the terms "first," "second," and the like, herein do not denote any order, quantity, or importance, but rather are used to distinguish one element/circuit/feature from another.

Notably, the limitations of the claims are not written in means-plus-function format or step-plus-function format. It is applicant's intention that none of the limitations be interpreted pursuant to 35 USC § 112, ¶6 or § 112(f), unless such claim limitations expressly use the phrase "means for" or "step for" followed by a statement of function and is void of any specific structure.

Again, there are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations.

What is claimed is:

1. A method of monitoring a Client, having an ethnicity, a culture and/or a socioeconomic status, via an MIA process using an MIA device, the method comprising:
   presenting first predetermined images, statements, music, and/or questions, via the MIA device, to the Client associated with the MIA device, while the Client is alone, wherein the first predetermined images, statements, music, and/or questions are dependent on the ethnicity, culture and/or socioeconomic status of the Client;
   acquiring first video and/or audio data, via the MIA device, of the Client's responses to the first predetermined images, statements, music, and/or questions presented to the Client via the MIA device;
   analyzing the first video and/or audio data, and/or changes therein, via the MIA process using the MIA device, to generate feedback data of the Client;
   determining second predetermined images, statements, music, and/or questions, via the MIA process using the MIA device, wherein the second predetermined images, statements, music, and/or questions are dependent on: (i) the ethnicity, culture and/or socioeconomic status of the Client, and (ii) the feedback data of the Client; and
   presenting the second predetermined images, statements, music, and/or questions, via the MIA device, to the Client associated with the MIA device.

2. The method of claim 1 wherein:
   acquiring the first video and/or audio data, via the MIA device, of the Client's responses further includes acquiring video data of the Client's facial responses to the predetermined images, statements, music, and/or questions presented to the Client via the MIA device.

3. The method of claim 2 wherein:
   analyzing the first video and/or audio data, and/or changes therein, to detect the state of the Client further includes a Core Group grading the Client's facial responses to the first predetermined images, statements, music, and/or questions presented to the Client via the MIA device; and the method further includes:
      acquiring second video and/or audio data, via the MIA device, of the Client's responses to the second predetermined images, statements, music, and/or questions presented to the Client via the MIA device; and
      determining a course of action, via a Core Group associated with the Client, for treatment of the Client based on: (i) the first video data, and/or changes therein, of the Client's responses and (ii) the second video and/or audio data, and/or changes therein, of the Client's responses.

4. The method of claim 1 wherein:
   acquiring the first video and/or audio data, via the MIA device, of the Client's responses further includes acquiring audio data of the Client's verbal responses to the first predetermined images, statements, music, and/or questions presented to the Client via the MIA device.

5. The method of claim 4 wherein:
   analyzing the first video and/or audio data, and/or changes therein, to detect the state of the Client further includes a Core Group grading the Client's verbal responses to the first predetermined images, statements, music, and/or questions presented to the Client via the MIA device; and the method further includes:
      acquiring second video and/or audio data, via the MIA device, of the Client's responses to the second predetermined images, statements, music, and/or questions presented to the Client via the MIA device; and
      determining a course of action, via a Core Group associated with the Client, for treatment of the Client based on: (i) the first audio data, and/or changes therein, of the Client's responses and (ii) the second video and/or audio data, and/or changes therein, of the Client's responses.

6. The method of claim 5 wherein:
   the verbal responses of the Client include tone, frequency and/or pattern, and/or changes therein.

7. The method of claim 1 wherein:
   acquiring the first video and/or audio data, via the MIA device, of the Client's responses further includes acquiring video data and audio data of the Client's facial and voice responses, respectively, to the first predetermined images, statements, music, and/or questions presented to the Client via the MIA device.

8. The method of claim 7 wherein:

analyzing the first video and/or audio data, and/or changes therein, to the detect the state of the Client further includes a Core Group grading the Client's facial responses and voice responses to the predetermined images, statements, music, and/or questions presented to the Client via the MIA device; and the method further includes:

acquiring second video and/or audio data, via the MIA device, of the Client's responses to the second predetermined images, statements, music, and/or questions presented to the Client via the MIA device; and determining a course of action, via a Core Group associated with the Client, for treatment of the Client based on: (i) the first video and/or audio data, and/or changes therein, of the Client's responses and (ii) the second video and/or audio data, and/or changes therein, of the Client's responses.

9. The method of claim 8 wherein:

the verbal responses of the Client include tone, frequency and/or pattern, and/or changes therein.

10. A system for monitoring a Client, having an ethnicity, a culture and/or a socioeconomic status, via an MIA process comprising:

an MIA device, having a display, a plurality of sensors, processing circuitry, and transmitting circuitry, to present a plurality of predetermined images, statements, music, and/or questions to the Client associated with the MIA device, while the Client is alone, wherein:

first predetermined images, statements, music, and/or questions are dependent on the ethnicity, culture and/or socioeconomic status of the Client, and second predetermined images, statements, music, and/or questions are dependent on: (i) the ethnicity, culture and/or socioeconomic status of the Client and (ii) feedback data of the Client to responses to the first predetermined images, statements, music, and/or questions, and wherein:

the plurality of sensors acquire video and/or audio data of the Client's responses to the plurality of predetermined images, statements, music, and/or questions presented to the Client via the MIA device; and the processing circuitry, is coupled to the plurality of sensors, to: (i) receive the video and/or audio data of the Client's responses to the first predetermined images, statements, music, and/or questions, and (ii) process the video and/or audio data to:

(a) generate the feedback data of the Client using the video and/or audio data of the Client's responses to the first predetermined images, statements, music, and/or questions, and (b) determine the second predetermined images, statements, music, and/or questions, wherein the second predetermined images, statements, music, and/or questions are dependent on: (1) the ethnicity, culture and/or socioeconomic status of the Client, and (2) the feedback data of the Client to responses to the first predetermined images, statements, music, and/or questions; and a computer, coupled to the processing circuitry and separate from the MIA device, to present the processed video and/or audio data to a Core Group associated with the Client, wherein based thereon, the Core Group analyzes the video and/or audio data of the Client's responses to the first and second predetermined images, statements, music, and/or questions, and/or changes therein, to the detect a state of the Client.

11. The system of claim 10 wherein, the computer further includes:

transmission circuitry to transmit data, representative of a treatment, determined by the Core Group associated with the Client based on the analysis of the video and/or audio data of the Client's responses to the first and second predetermined images, statements, music, and/or questions to the detect the state of the Client, to the MIA device.

12. The system of claim 10 wherein, the computer further includes:

transmission circuitry to transmit data, representative of a treatment, determined by the Core Group associated with the Client based on the analysis of the video and/or audio data of the Client's responses to the first and second predetermined images, statements, music, and/or questions to the detect the state of the Client, to a second computer which is associated with a member of the Core Group that is local to the MIA device and Client.

13. The system of claim 10 wherein:

the MIA device acquires video data of the Client's facial responses to the first predetermined images, statements, music, and/or questions presented to the Client via the MIA device, and the processing circuitry receives the video data of the Client's facial responses to the first predetermined images, statements, music, and/or questions and processes the video data of the Client's facial responses to the first predetermined images, statements, music, and/or questions, and the computer presents the processed video data to a Core Group associated with the Client.

14. The system of claim 13 wherein:

the computer further includes transmission circuitry to transmit to the MIA device grading data, which is representative of a data of grading, via the Core Group, of the Client's facial responses to the first and second predetermined images, statements, music, and/or questions presented to the Client.

15. The system of claim 10 wherein:

the MIA device acquires audio data of the Client's verbal responses to the first predetermined images, statements, music, and/or questions presented to the Client via the MIA device, and the processing circuitry receives the audio data of the Client's verbal responses to the first predetermined images, statements, music, and/or questions and process the audio data of the Client's verbal responses to the first predetermined images, statements, music, and/or questions, and the computer presents the processed audio data to a Core Group associated with the Client.

16. The system of claim 15 wherein:

the computer further includes transmission circuitry to transmit to the MIA device grading data, which is representative of a data of grading, via the Core Group, of the Client's verbal responses to the first and second predetermined images, statements, music, and/or questions presented to the Client.

17. The system of claim 16 wherein:

the verbal responses of the Client include tone, frequency and/or pattern, and/or changes therein.

18. The system of claim 10 wherein:
the computer further includes transmission circuitry to transmit data, representative of a treatment, determined by the Core Group associated with the Client based on the analysis of the verbal data of the Client's responses to the first and second predetermined images, statements, music, and/or questions to a second computer which is associated with a member of the Core Group that is local to the MIA device and Client.

19. A method of monitoring a Client, having an ethnicity, a culture and/or a socioeconomic status, via an MIA process using an MIA device, the method comprising:
authenticating the Client via facial, voice and/or biometric data;
enabling the MIA process using the MIA device in response to authenticating the Client;
presenting first predetermined statements, music, and/or questions, via the MIA device, to the Client associated with the MIA device, wherein the first predetermined statements, music, and/or questions are dependent on the ethnicity, culture and/or socioeconomic status of the Client;
acquiring first video and/or audio data, via the MIA device, of the Client's responses to the first predetermined statements, music, and/or questions presented to the Client via the MIA device;
generating feedback data, via the MIA process using the MIA device, based on the first video and/or audio data of the Client's responses to the first predetermined statements, music, and/or questions presented to the Client via the MIA device;
determining second predetermined statements, music, and/or questions, via the MIA process using the MIA device, wherein the second predetermined statements, music, and/or questions are dependent on: (i) the ethnicity, culture and/or socioeconomic status of the Client, and (ii) the feedback data generated by the MIA process using the MIA device;
presenting the second predetermined statements, music, and/or questions, via the MIA device, to the Client associated with the MIA device; and
analyzing the first and second video and/or audio data, and/or changes therein, to detect a state of the Client wherein the analyzing the video and/or audio data are dependent on the ethnicity, culture and/or socioeconomic status of the Client.

20. The method of claim 19 further including:
determining a course of action, via a Core Group associated with the Client, for treatment of the Client based on the analysis of the first and second video and/or audio data, and/or changes therein.

* * * * *